United States Patent
Loughner et al.

(10) Patent No.: US 7,820,595 B2
(45) Date of Patent: Oct. 26, 2010

(54) PENOXSULAM AS A TURFGRASS, VINEYARD AND ORCHARD FLOOR HERBICIDE

(75) Inventors: Daniel L. Loughner, Huntingdon Valley, PA (US); Anita L. Alexander, Lawrenceville, GA (US); Toshiya Ogawa, Indianapolis, IN (US); James M. Breuninger, Zionsville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 142 days.

(21) Appl. No.: 12/252,007

(22) Filed: Oct. 15, 2008

(65) Prior Publication Data

US 2009/0042728 A1    Feb. 12, 2009

Related U.S. Application Data

(62) Division of application No. 11/351,784, filed on Feb. 10, 2006.

(60) Provisional application No. 60/652,292, filed on Feb. 11, 2005.

(51) Int. Cl.
 *A01N 43/90* (2006.01)
 *A01N 43/82* (2006.01)
(52) U.S. Cl. ................. 504/241; 504/263
(58) Field of Classification Search ............. 504/241, 504/263
 See application file for complete search history.

(56) References Cited

U.S. PATENT DOCUMENTS

| 5,858,924 A * | 1/1999 | Johnson et al. ............. 504/241 |
| 6,613,718 B2 | 9/2003 | Gupta et al. |
| 2006/0183638 A1 | 8/2006 | Loughner |
| 2007/0010397 A1 | 1/2007 | Goto et al. |
| 2007/0197391 A1 | 8/2007 | Clark et al. |

OTHER PUBLICATIONS

The Agrochemicals Handbook, 3ed, AQ433/Aug 91, AO111/Aug 91, AO133/Aug 91, A0278/Aug 91, A0530/Aug 91.*
PCT Search Report PCT/US2006/004750, Apr. 27, 2007, Daniel L. Loughner, et al.
Anonymous; "462055 2-(2,2-difluoroethoxy)-6-trifluoromethyl-*N*-(5,8-dimethoxy[1,2,4]triazolo[1,5-c]pyrimidin-2-yl)benzenesulfonamide and its use as herbicide in mixtures;" Reseach Disclosure Journal; Oct. 2002; pp. 1832-1833.
University of GA Coop Ext Service, Postemergence of Broadleaf Weed Control with Penoxsulam (Feb. 26, 2004).
University of GA Coop Ext Service, Tolerance of 'Ky 31' Tall Fescue to Penoxsulam (Jul. 8, 2004).
Anonymous; "IPCOM000116219D: Penoxsulam and its use as aherbicide in mixtures for use in rice, wheat, barley, oats, sorghum, corn, maize, IVM, rangeland, pastures, grasslands, fallowland, turf and aquatics;" The IP.com Journal; (Published at IP.com on Mar. 30, 2005) Published in the IP.com Journal on Apr. 2005; pp. 286-293; vol. 5 No. 4; IP.com, Inc.; West Henrietta, NY USA.

* cited by examiner

*Primary Examiner*—Alton N Pryor
(74) *Attorney, Agent, or Firm*—Craig E. Mixan

(57) ABSTRACT

Penoxsulam, 2-(2,2-difluoroethoxy)-N-(5,8-dimethoxy[1,2,4]-triazolo[1,5-c]pyrimidin-2-yl)-6-(trifluoromethyl)benzenesulfonamide, provides synergistic herbicidal control with dicamba, the mixture of 2,4-D, triclopyr and clopyralid, or the mixture of 2,4-D and mecoprop-P.

1 Claim, No Drawings

PENOXSULAM AS A TURFGRASS, VINEYARD AND ORCHARD FLOOR HERBICIDE

This application is a divisional application of U.S. patent application Ser. No. 11/351,784 filed on Feb. 10, 2006.

BACKGROUND OF THE INVENTION

This invention relates to a method of controlling broadleaf weeds in turf, vineyards and orchards using an herbicidally effective amount of penoxsulam, 2-(2,2-difluoroethoxy)-N-(5,8-dimethoxy[1,2,4]triazolo[1,5-c]-pyrimidin-2-yl)-6-(trifluoromethyl)benzenesulfonamide.

The search for compounds which have a combination of excellent herbicidal activity towards target weeds and low toxicity towards non-target plants is a continuing one because of factors such as the desire for compounds exhibiting greater activity, better selectivity, lower undesirable environmental impact, lack of phytotoxicity to the locus of application, lower production and market cost and higher effectiveness against weeds resistant to known herbicides. In particular, there exists a need for effective control of broadleaf weeds in turfgrass and in trees and vines. Commercial herbicides, for example, 2,4-D, mecoprop-P, clopyralid, triclopyr and methylarsonic acid, have serious deficiencies such as requiring a high application rate to be effective, possessing less than desirable environmental profiles, having too great or too poor soil mobility and/or being toxic to non-target plants and or the turfgrass species.

SUMMARY OF THE INVENTION

It has now been found that penoxsulam, 2-(2,2-difluoroethoxy)-N-(5,8-dimethoxy[1,2,4]triazolo[1,5-c]pyrimidin-2-yl)-6-(trifluoromethyl) benzenesulfonamide, is an effective herbicide for controlling broadleaf weeds in turfgrass, vineyards and orchards. The invention concerns a method for controlling undesirable vegetation in turfgrass, vineyards and orchards which comprises contacting the vegetation or the locus thereof with, or applying to the soil to prevent the emergence or subsequent growth of vegetation, a herbicidally effective amount of penoxsulam.

For turf applications, the invention includes herbicidal compositions comprising an herbicidally effective amount of a) penoxsulam in admixture with an agriculturally acceptable adjuvant or carrier and b) a fertilizer. Particularly effective compositions of penoxsulam and fertilizer are granule compositions having an average particle size of from about 0.5 millimeters (mm) to about 2.5 mm. These compositions are preferentially applied as dry product.

DETAILED DESCRIPTION OF THE INVENTION

Penoxsulam, 2-(2,2-difluoroethoxy)-N-(5,8-dimethoxy-[1,2,4]triazolo[1,5-c]pyrimidin-2-yl)-6-(trifluoromethyl) benzenesulfonamide, and its preparation have been described in U.S. Pat. No. 5,858,924. Both this patent and *The Pesticide Manual*, 13$^{th}$ Ed., describe penoxsulam as a particularly effective rice herbicide.

Penoxsulam has now been found to be useful in controlling broadleaf weeds and sedges in turfgrass and in vine and orchard floors. Penoxsulam is particularly effective against most important weeds in these applications, viz., white clover, *Trifolium repens* L. (TRFRE); buckhorn plantain, *Plantago lanceolata* L. (PLALA); dandelion, *Taraxacum officinale* (TAROF); broadleaf plantain, *Plantago major* L. (PLAMA); ground ivy, *Glechoma hederacea* L. (GLEHE); common lespedeza, *Lespedeza striata* (LESST); pennywort (dollarweed), *Hydrocotyle* spp (HYDSS); Virginia buttonweed, *Diodia virginiana* L. (DIQVI); English daisy, *Bellis perennis* L. (BELPE); and yellow nutsedge, *Cypres esculentus* L. (CYPES).

At rates herbicidally effective against these weeds, penoxsulam causes acceptable or no damage to mature, well-established Bermudagrass, creeping bentgrass, red fescue, tall fescue, perennial ryegrass, zoysiagrass, centipedegrass, St. Augustinegrass and Kentucky bluegrass.

In vine and orchard floor applications, penoxsulam has been shown to be effective in controlling Windgrass, *Apera spica-venti* (APESV); redroot pigweed, *Amaranthus retroflexus* (AMARE); common purslane, *Portulaca oleracea* (POROL); giant foxtail, *Setaria faberi* (SETFA); barnyardgrass, *Echinochloa crus-galli* (ECHCG); junglerice, *Echinochloa colonum* (ECHCO); london rocket, *Sisymbrium irio* (SSYIR); wild mustard, *Sinapsis arvense* (SINAR); sun spurge, *Euphorbia helioscopia* (EPHHE); redstem filaree, *Erodiuam cicutarium* (EROCI); common mallow, *Malva neglecta* (MALNE); little mallow, *Malva parviflora* (MALPA); annual sowthistle, *Sonchus oleraceus* (SONOL); and common groundsel, *Senecio vulgaris* (SENVU).

The term herbicide is used herein to mean an active ingredient that kills, controls or otherwise adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation include emerging seedlings and established vegetation.

Herbicidal activity is exhibited by penoxsulam when it is applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific adjuvants and carriers employed, the soil type, and the like, as well as the amount of chemical applied. These and other factors can be adjusted as is known in the art to promote non-selective or selective herbicidal action. Generally, it is preferred to apply penoxsulam postemergence in turf to relatively immature undesirable vegetation. In orchard floor applications, penoxsulam can be applied pre-emergence, as well as postemergence to relatively immature undesirable vegetation, to achieve the maximum control of weeds.

Application rates of about 5 to about 280 grams of active ingredient per hectare (gai/Ha) are generally employed in postemergence operations with about 20 to about 180 gai/Ha being preferred; for preemergence applications, rates of about 4 to about 140 gai/Ha are generally employed with about 9 to about 70 gai/Ha being preferred.

Penoxsulam is often best applied in conjunction with one or more other herbicides to obtain control of a wider variety of undesirable vegetation. When used in conjunction with other herbicides, penoxsulam can be formulated with the other herbicide or herbicides, tank mixed with the other herbicide or herbicides, or applied sequentially with the other herbicide or herbicides. Some of the herbicides that can be employed in conjunction with penoxsulam include 2,4-D, 2,4-DP, 2,4-DB, acetochlor, aciflurofen, aclonifen, alachlor, amiprofos-methyl, aminopyralid, ametryn, aminotriazole, ammonium thiocyanate, asulam, atrazine, azimsulfuron, benefin, benfluralin, benfuresate, bensulide, Bentazon, bethrodine, bialaphos, bifenox, bispyribac-sodium, bromacil, bromoxynil, butafenacil, butamifos, butralin, cafenstrole, carbetamide, carfentrazone, carfentrazone-ethyl, clethodim, cloransulam, chlorphthalim, chlorpropham, chlorsulfuron, chlorflurenol, chlorthal-dimethyl, chlorthiamid, cinmethylin, cinosulfuron, clopyralid, clomazone, cumyluron, cyanazine, cyclosulfamuron, cycloxydim, DCPA, dicamba, dichlobenil, diclofop, dithiopyr, dichlorprop-P, diclosulam, diflufenican, diflufenzopyr, diquat, diuron, DSMA, endothal-disodium, EPTC, ET-751, ethofumesate, ethoxysulfuron, flazasulfuron, florasulam, flazasulfuron, flucetosulfuron, flumetsulam, foramsulfuron, fluazifop, fluazifop-P-butyl, flucetosulfuron, flufenacet, flumioxazin, flupoxam, flupyrsulfuron, fluroxypyr, glufosinate, glufosinate-ammonium, glyphosate, haloxyfop-methyl, halosulfuron, hexazinone, imazaquin-ammonium, imazethapyr, imazosulfuron, indanofan, iodosulfuron, ioxynil, isoproturon, iodosulfuron, isoxaben, isoxaflutole, imazamox, imazapyr, imazaquin, imazapic, kerbutilate, KIH-485, lenacil, MCPA, mecoprop-P, MCPP, MSMA, mesosulfuron, mesotrione, methyl daimuron, metolachlor, metribuzin, metsulfuron, metsulfuron-methyl, napropamide, nicosulfuron, norflurazon, orthobencarb, orthosulfamuron, oryzalin, oxadiargyl, oxadiazon, oxaziclomefone, oxyfluorfen, paraquat, pebulate, pendimethalin, picolinafen, picloram, pinoxaden, primisulfuron, prodiamine, prosulfuron, profluazol, propoxycarbazone, propyzamide, prosulfocarb, prodiamine, pyrazone, pyrazosulfuron-ethyl, pyributicarb, pyrithiobac, pyraflufen-ethyl, pyrimisulfan, quinoclamine, quinclorac, quizalofop-ethyl-D, rimsulfuron, sethoxydim, siduron, simazine, sulfentrazone, sulfosate, sulfosulfuron, sulfometuron, tebuthiuron, terbacil, thenylchlor, thiazopyr, thifensulfuron, topramezone, tralkoxydim, triclopyr, trifluralin, trifloxysulfuron-sodium, tritosulfuron, triaziflam and N-(5,7-dimethoxy[1,2,4]triazolo[1,5-a]pyrimidin-2-yl)-2-methoxy-4-(trifluoromethyl)-3-pyridinesulfonamide. It is generally preferred to apply penoxsulam and other complementary herbicides at the same time, either as a combination formulation or as a tank mix. When applying in this way, synergistic responses have been observed specific to species and mixture.

Penoxsulam can also be applied with herbicide safeners such as benoxacor, benthiocarb, cloquintocet, cyometrinil, daimuron, dichlormid, dicyclonon, fenchlorazole-ethyl, fenclorim, flurazole, fluxofenim, furilazole, isoxadifen-ethyl, mefenpyr-diethyl, MG191, MON4660, oxabetrinil, R29148 and N-phenylsulfonylbenzoic acid amides.

While it is possible to utilize penoxsulam directly as an herbicide, it is preferable to use it in mixtures containing a herbicidally effective amount of penoxsulam along with at least one agriculturally acceptable adjuvant or carrier. Suitable adjuvants or carriers should not react chemically with penoxsulam or other composition ingredients. Such mixtures can be designed for application directly to weeds or their locus or can be concentrates or formulations that are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, glycerine, ammonium sulfate solutions or ammonium nitrate solutions and the like. Water is generally the carrier of choice for the dilution of concentrates.

Suitable solid carriers include talc, pyrophyllite clay, silica, attapulgus clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, granule fertilizer and the like.

It is usually desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Typical surface-active agents include salts of alkyl sulfates, such as diethanolammonium lauryl sulfate; alkylarylsulfonate salts, such as calcium dodecyl-benzenesulfonate; alkylphenol-alkylene oxide addition products, such as polyoxyethylene (9) nonylphenol ether; alcohol-alkylene oxide addition products, such as polyoxyethylene (8) tridecyl ether; soaps, such as sodium stearate; alkyl-naphthalenesulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly used in agricultural compositions include compatibility agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulators, fungicides, insecticides, and the like and can be formulated with liquid fertilizers or solid, particulate fertilizer carriers such as ammonium nitrate, urea and the like that are used to deliver nutrients to turfgrass.

Nitrogen based fertilizers are routinely used in turfgrass management to feed grass and stimulate growth. Surprisingly, penoxsulam, when delivered on a granule nitrogen fertilizer or one that contains nitrogen, phosphorus or potassium, gave unexpected weed control that was superior to commercial granule standards. These penoxsulam formulations provided better consistency and spectrum of weed control and were less injurious than liquid applications of penoxsulam. In general, smaller fertilizer granule carriers provided more effective weed control than larger granules. Particularly effective compositions of penoxsulam and fertilizer are granule compositions having an average particle size of from about 0.5 millimeters (mm) to about 2.5 mm and applied as dry product. More preferably, the granule compositions have an average particle size of from about 0.75 mm to about 2.15 mm. Most preferably, the granule compositions have an average particle size of from about 0.75 mm to about 1.25 mm. Such a granule is prepared by spraying an aqueous suspension of pulverized penoxsulam on to a bed of fertilizer granules, under efficient flowing conditions. A solution of penoxsulam in an organic solvent may be used as alternative spray liquor. The water or the organic solvent used as diluent may be removed by heating and/or vacuum drying, if desired. If the granule gets sticky due to residual moisture, a small amount of absorbent, such as amorphous silica, may be added to keep granule free-flowing.

The concentration of penoxsulam in the herbicidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to weeds, the locus of weeds, or to the soil, generally contain about 0.0001 to about 1 weight percent active ingredient and preferably contain about 0.001 to about 0.05 weight percent.

The present compositions can be applied to weeds or their locus by the use of conventional ground or aerial dusters, sprayers, and granule applicators, by addition to irrigation water, and by other conventional means known to those skilled in the art.

The following Examples are presented to illustrate the various aspects of this invention and should not be construed as limitations to the claims.

EXAMPLES

Preparation of Penoxsulam Fertilizer Granules

A 50% aqueous suspension concentrate of penoxsulam was at first prepared: Penoxsulam was dispersed in water, in the presence of surfactants and other inert ingredients, and pulverized by means of bead-milling until an average particle size of 2 to 5 micrometer was achieved. The milled concentrate was diluted with water and sprayed on to a bed of fertilizer granules in a tumbler to obtain a final formulation product.

Example 1

Penoxsulam 0.05% 46-0-0 Urea Granule

In a tumbler, 2,490 grams of 46-0-0 urea granule of average particle size of 2.15 mm, and 3.75 grams of amorphous silica absorbent were added. Tumbler was run at a speed that enabled a good flow of the granules. In an atomizer, 2.5 grams of the 50% penoxsulam milled concentrate (1.25 grams penoxsulam) and 3.75 grams of water were added. The diluted suspension of penoxsulam was sprayed onto the granules. The obtained granules were assayed and found to contain 0.052% penoxsulam.

Example 2

Penoxsulam 0.05% 28-4-12 Mixed Fertilizer Granule

In a tumbler, 2,490 grams of 28-4-12 mixed granule of average particle size of 0.75 mm, and 3.75 grams of amorphous silica absorbent were added. Tumbler was run at a speed that enabled a good flow of the granules. In an atomizer, 2.5 grams of the 50% penoxsulam milled concentrate (1.25 grams penoxsulam) and 3.75 grams of water were added. The diluted suspension of penoxsulam was sprayed onto the granules. The obtained granules were assayed and found to contain 0.048% penoxsulam.

Example 3

Penoxsulam 0.01% 28-3-10 Mixed Fertilizer Granule

In a tumbler, 11,961 grams of 28-3-10 mixed fertilizer granules of average particle size of 1.5 mm was added. While running the tumbler, a liquid that consisted of 2.64 grams of penoxsulam 50% milled concentrate (penoxsulam 1.32 grams) and 18.0 grams of water was sprayed onto the granules from an atomizer. After the spraying, 18.0 grams of amorphous silica was added and incorporated with the granules. The obtained granules were assayed and found to contain 0.010% penoxsulam.

Postemergent Activity of Granule Herbicides

Field studies were conducted in established turfgrass sites containing a natural population of target broadleaf weeds. Replicated trials, containing a minimum of three replications and having individual plots ranging in size from 25 to 50 ft. sq (2.3 to 4.6 square meters), were initiated in the late spring when turf and weeds were actively growing. Granule treatments were uniformly applied to individual plots using a common hand-shaker method. Applications were made in the early morning when dew was present. Natural rainfall and supplemental irrigation were used to maintain healthy turf and active weed growth throughout the study period. Control of each weed species in the study site was made at 2, 4 and 8 weeks after treatment. Control was determined visually by comparing treated and untreated weeds and scored on a 0 to 100 percent scale where 0 corresponds to no control and 100 corresponds to complete kill.

Treatments evaluated, application rate employed, weed species evaluated and results are presented in the following Tables I-III.

TABLE I

Postemergent Broadleaf Weed Control
Granule Herbicides:

| | Mean Percent Weed Control (#Sites Used to Compute Mean) | | | | | | | |
|---|---|---|---|---|---|---|---|---|
| | 4 Weeks After Treatment | | | | 8 Weeks After Treatment | | | |
| Treatment[1] | PLALA (3) | TAROF (5) | TRFRE (8) | PLAMA (2) | PLALA (3) | TAROF (5) | TRFRE (7) | PLAMA (2) |
| Penoxsulam | 53 | 93 | 93 | 81 | 62 | 87 | 94 | 87 |
| Scotts Plus 2 | 53 | 71 | 59 | 70 | 63 | 68 | 60 | 69 |
| Trimec | 48 | 55 | 64 | 58 | 41 | 58 | 64 | 68 |

[1]Application Rates
Penoxsulam: 140 gai/Ha (0.125 lb ai/A)
Scotts Plus 2: 1682 gae/Ha (1.5 lb ae/a) 2,4-D plus 841 gae/Ha (0.75 pound ae/A) mecoprop-P
Trimec: 1121 gae/ha (1.0 lb ae/A) 2,4-D plus 516 gae/Ha (0.46 lb ae/A) mecoprop-P plus 112 gae/Ha (0.1 lb ae/A) dicamba

TABLE II

Postemergent Broadleaf Weed Control
Granule Herbicides:

| | | Mean Percent Weed Control (# Sites Used to Compute Mean) | | | |
|---|---|---|---|---|---|
| | | 4 WAT | | 8 WAT | |
| Treatment[1] | | TAROF (3) | TRFRE (5) | TAROF (3) | TRFRE (5) |
| Penoxsulam GR | A | 61 | 54 | 39 | 54 |
| | B | 71 | 72 | 59 | 68 |
| | C | 73 | 95 | 63 | 94 |
| Scotts Plus 2 | | 74 | 42 | 47 | 41 |

[1]Application Rates
Penoxsulam A: 11.2 gai/Ha (0.01 lb ai/A)
Penoxsulam B: 22.4 gai/Ha (0.02 lb ai/A)
Penoxsulam C: 44.9 gai/Ha (0.04 lb ai/A)
Scotts Plus 2: 1682 gae/Ha (1.5 lb ae/a) 2,4-D plus 841 gae/Ha (0.75 pound ae/A) mecoprop-P

TABLE III

Postemergent Broadleaf Weed Control
Granule Herbicides

| | Mean Percent Weed Control (#Sites Used to Compute Mean) | | | | | | | |
|---|---|---|---|---|---|---|---|---|
| | 4 Weeks After Treatment | | | | 8 Weeks After Treatment | | | |
| Treatment[1] | TRFRE (8) | TAROF (6) | DIQVI (1) | HYDSS (1) | TRFRE (8) | TAROF (6) | DIQVI (1) | HYDSS (1) |
| Penoxsulam A | 85 | 45 | 67 | 50 | 74 | 25 | 48 | 40 |
| Penoxsulam B | 94 | 61 | 76 | 97 | 88 | 45 | 63 | 93 |
| Penoxsulam C | 96 | 61 | 93 | 98 | 91 | 47 | 87 | 84 |
| Penoxsulam D | 96 | 69 | 92 | 100 | 97 | 57 | 78 | 97 |
| Trimec | 55 | 58 | 15 | 15 | 56 | 45 | 10 | 24 |

[1]Application Rates
Penoxsulam A: 22.4 gai/Ha (0.02 lb ai/A)
Penoxsulam B: 44.9 gai/Ha (0.04 lb ai/A)
Penoxsulam C: 67.3 gai/Ha (0.06 lb ai/A)
Penoxsulam D: 100 gai/Ha (0.09 lb ai/A)
Trimec: 1121 gae/ha (1.0 lb ae/A) 2,4-D plus 516 gae/Ha (0.46 lb ae/A) mecoprop-P plus 112 gae/Ha (0.1 lb ae/A) dicamba Improved Turf Tolerance with Granule Herbicides Turf tolerance studies were conducted in monoculture stands of perennial ryegrass, tall fescue and St. Augustinegrass. Replicated trials, containing a minimum of three replications and having individual plots ranging in size from 25 to 50 ft. sq (2.3 to 4.6 square meters), were initiated in the late spring when turf was actively growing. Granule (GR) treatments were uniformly applied to individual plots using a common hand-shaker method while liquid (2SC) applications were made with a backpack sprayer calibrated to deliver a liquid volume between 40 and 60 gallons per acre (338 to 507 liters per hectare) at an operating pressure of 40 to 60 psi (275 to 413 kilopascals). Natural rainfall and supplemental irrigation, fertilizer, fungicides and insecticides were used to maintain healthy turf throughout the study period. Turf tolerance evaluations were made weekly for 8 weeks after application. Evaluations compared treated and untreated plot areas and consisted of one or all of the following evaluations: 1) visual estimate of turf injury made on a 0 to 10 scale with 0 indicating no visible injury symptoms, 10 being dead turf and 3 or less being commercially acceptable; 2) visual estimate of turf color made on a 0 to 10 scale with 0 being brown to dead turf, 10 being a lush green turf of highest quality and 6.5 being commercially acceptable; 3) visual estimate of turf density made on a 0 to 100 scale with 0 being bare ground, 100 being a thick solid stand of highest quality and 90 percent density being commercially acceptable.

Treatments evaluated, application rate employed, turf species evaluated and results are presented in the following Tables IV-VI.

TABLE IV

Perennial Ryegrass Tolerance to Penoxsulam Formulations:
Results 3-4 Weeks After Treatment

| | | Turf Tolerance Evaluations (14 Data Points used to Compute Mean) | | |
|---|---|---|---|---|
| Treatment[1] | | Injury | Color | Density |
| Penoxsulam 2SC | A | 2.2 | 7.4 | 88 |
| | B | 2.6 | 7.1 | 88 |
| | C | 3.6 | 7.2 | 81 |
| Penoxsulam GR | A | 0.8 | 9 | 100 |
| | B | 0.9 | 8.4 | 100 |
| | C | 2.8 | 7.8 | 93 |

[1]Application Rates
Penoxsulam A: 16.8 gai/Ha (0.015 lb ai/A)
Penoxsulam B: 33.6 gai/Ha (0.03 lb ai/A)
Penoxsulam C: 67.3 gai/Ha (0.06 lb ai/A)

TABLE V

Tall Fescue Tolerance to Penoxsulam Formulations:
Results 1-2 Weeks After Treatment

| Treatment[1] | | Turf Tolerance Evaluations (15 Data Points used to Compute Mean) Injury |
|---|---|---|
| Penoxsulam 2SC | A | 2.2 |
|  | B | 2.8 |
|  | C | 3.0 |
| Penoxsulam GR | A | 1.4 |
|  | B | 2.1 |
|  | C | 2.4 |

[1]Application Rates
Penoxsulam A: 44.9 gai/Ha (0.04 lb ai/A)
Penoxsulam B: 89.7 gai/Ha (0.08 lb ai/A)
Penoxsulam C: 135 gai/Ha (0.12 lb ai/A)

TABLE VI

St. Augustinegrass Tolerance to Penoxsulam Formulations:
Results 1-2 Week After Treatment

| Treatment[1] | | Turf Tolerance Evaluations (11 Data Points used to Compute Mean) | | |
|---|---|---|---|---|
| | | Injury | Color | Density |
| Penoxsulam 2SC | A | 1.1 | 4.4 | 86 |
|  | B | 1.2 | 4.1 | 89 |
|  | C | 2.2 | 3.5 | 83 |
| Penoxsulam GR | A | 0.2 | 6.6 | 93 |
|  | B | 1.0 | 6.5 | 96 |
|  | C | 1.0 | 5.8 | 93 |

[1]Application Rates
Penoxsulam A: 44.9 gai/Ha (0.04 lb ai/A)
Penoxsulam B: 89.7 gai/Ha (0.08 lb ai/A)
Penoxsulam C: 135 gai/Ha (0.12 lb ai/A)

The Effect of Granule Particle Size on the Performance of Penoxsulam.

Greenhouse and field studies evaluated the effect of two granule carriers and two particles sizes on the postemergent broadleaf activity of penoxsulam. The two carriers were a 46-0-0 and 28-4-12 fertilizer blend and the particle sizes averaged 0.75 mm and 2.15 mm.

Field studies were conducted in established turfgrass sites containing a natural population of target broadleaf weeds. Replicated trials, containing a minimum of three replications and having individual plots ranging in size from 25 to 50 ft. sq (2.3 to 4.6 square meters), were initiated in the late spring when turf and weeds were actively growing. Granule treatments were uniformly applied to individual plots using a common hand-shaker method. Applications were made in the early morning when dew was present. Natural rainfall and supplemental irrigation were used to maintain healthy turf and active weed growth throughout the study period. Control of each weed species in the study site was made at 2, 4 and 8 weeks after treatment. Control was determined visually by comparing treated and untreated weeds and scored on a 0 to 100 percent scale where 0 corresponds to no control and 100 corresponds to complete kill.

Greenhouse studies were applied both post and pre-emergence to broadleaf weeds and sedge reared from seed or nutlet in 12.7" (32.25 cm) by 8.8" (22.35 cm) flats of a loam soil. Particle size and carrier were evaluated post emergence, carrier comparisons with the smaller particle size of 0.75 was evaluated pre-emergence. Stage of growth of species at post emergence application:

PLAMA and TAROF in the 3 to 5 leaf stage, TRFRE in the $3^{rd}$ tri-foliate stage and CYPES in the 3 to 4 leaf stage. Post emergence trial design was a replicated block, one species per flat, 3 replicate flats per treatment. Granule treatments were uniformly applied to individual flats on an area basis using a common hand-shaker method. Post emergence applications were made to the flat covering both soil and misted foliage. Trial was sub-irrigated daily, and watered over the top 1 time per week starting 7 days after application to simulate a natural rainfall event. Active weed growth was maintained throughout the study period. Weed control of each species in the post emergence study was assessed at 2, 3 and 4 weeks after treatment. Pre-emergence trial design was 2 species per flat, 4 replicate flats, block design. Pre-emergence applications were made to the soil surface using a common hand shaker method on an area basis. Overhead irrigation was maintained throughout the trial. Weed control of each species in the pre-emergence study was assessed at 2, 3, 4 and 5 weeks after application. Control was determined visually by comparing treated and untreated flats and scored on a 0 to 100 percent scale where 0 corresponds to no control and 100 corresponds to complete kill. Treatments evaluated, application rate employed, weed species evaluated and results are presented in the following Tables VII-IX.

TABLE VII

Postemergent Broadleaf Weed/Sedge Control
Penoxsulam Granule/Particle Size Comparison Greenhouse Results

| Carrier | Particle Size (mm) | Appl Rate gai/Ha (lb ai/A) | Percent Weed Control 27-30 DAA | | | |
|---|---|---|---|---|---|---|
| | | | TRFRE | TAROF | PLAMA | CYPES |
| 46-0-0 | 0.75 | 5.6 (0.005) | 22 | 55 | 47 | 18 |
| | | 11.2 (0.01) | 58 | 67 | 77 | 30 |
| | | 22.4 (0.02) | 72 | 98 | 97 | 65 |
| 46-0-0 | 2.15 | 5.6 (0.005) | 5 | 23 | 8 | 3 |
| | | 11.2 (0.01) | 33 | 48 | 15 | 20 |
| | | 22.4 (0.02) | 37 | 60 | 50 | 42 |
| 28-4-12 | 0.75 | 5.6 (0.005) | 40 | 50 | 35 | 18 |
| | | 11.2 (0.01) | 57 | 88 | 75 | 37 |
| | | 22.4 (0.02) | 68 | 97 | 96 | 60 |
| 28-4-12 | 2.15 | 5.6 (0.005) | 12 | 23 | 0 | 37 |
| | | 11.2 (0.01) | 38 | 60 | 27 | 25 |
| | | 22.4 (0.02) | 58 | 68 | 38 | 35 |

TABLE VIII

Pre-emergent Broadleaf Weed/Sedge Control
Penoxsulam Granule Urea vs. NPK Greenhouse Results

| Carrier | Particle Size (mm) | Appl Rate gai/Ha (lb ai/A) | Percent Weed Control 35 DAA | | | |
|---|---|---|---|---|---|---|
| | | | TRFRE | TAROF | PLAMA | CYPES |
| 46-0-0 | 0.75 | 5.6 (0.005) | 55 | 77 | 76 | 37 |
| | | 11.2 (0.01) | 75 | 96 | 87 | 57 |
| | | 22.4 (0.02) | 98 | 96 | 94 | 79 |
| 28-4-12 | 0.75 | 5.6 (0.005) | 80 | 71 | 72 | 60 |
| | | 11.2 (0.01) | 98 | 96 | 82 | 70 |
| | | 22.4 (0.02) | 99 | 98 | 100 | 89 |

TABLE IX

Postemergent Broadleaf Weed Control
Penoxsulam Granule/Particle Size Comparison
Field Results

| Carrier | Particle Size (mm) | Appl Rate gai/Ha (lb ai/A) | Percent Weed Control 26-27 DAA TRFRE | Percent Weed Control 26-27 DAA HYDSS |
|---|---|---|---|---|
| 46-0-0 | 0.75 | 11.2 (0.01) | 82 | 44 |
|  |  | 22.4 (0.02) | 95 | 87 |
| 46-0-0 | 2.15 | 11.2 (0.01) | 34 | 38 |
|  |  | 22.4 (0.02) | 78 | 75 |
| X28-4-12 | 0.75 | 11.2 (0.01) | 80 | 56 |
|  |  | 22.4 (0.02) | 97 | 70 |
| 28-4-12 | 2.15 | 11.2 (0.01) | 48 | 49 |
|  |  | 22.4 (0.02) | 70 | 42 |

Post Emergent Synergistic Activity of Granule Herbicides

Field and greenhouse studies were conducted to determine if there may be any synergistic response when penoxsulam is combined with other herbicides for post emergence broadleaf or sedge control. Field studies were conducted in established turfgrass sites containing a natural population of target broadleaf weeds. Replicated trials, containing a minimum of three replications and having individual plots ranging in size from 25 to 50 ft. sq (2.3 to 4.6 square meters), were initiated in the late spring when turf and weeds were actively growing. Granule treatments were uniformly applied to individual plots using a common hand-shaker method. Applications were made in the early morning when dew was present. Natural rainfall and supplemental irrigation were used to maintain healthy turf and active weed growth throughout the study period.

Control of each weed species in the study site was made at 2, 4 and 8 weeks after treatment. Control was determined visually by comparing treated and untreated weeds and scored on a 0 to 100 percent scale where 0 corresponds to no control and 100 corresponds to complete kill.

Results based on average weed control from 2 studies 4 weeks after application. Component A was penoxsulam at 0.02 or 0.04 lb ai/A. Component B was dicamba at 0.1 lb ai/A. Individual products and mixture were applied on a 30-3-4 granule fertilizer formulated to deliver 116 pounds fertilizer per acre (129 kg per hectare). Loadings for the individual component on the fertilizer were:

Penoxsulam 22.4 gai/Ha (0.02 lb ai/A)=0.017%
Penoxsulam 44.9 gai/Ha (0.04 lb ai/A)=0.034%
Dicamba 112 gae/Ha (0.1 lb ai/A)=0.086%

For combinations the same loadings were applied to the same granule carrier and applied as a single product to test area.

Treatments, application rate employed and results for *Hydrocotyle* species (HYDSS) are presented in the following Table X.

TABLE X

Postemergent Broadleaf Weed Control
Penoxsulam + Dicamba Field Results

| Treatments | Rate in gai/Ha | % Control Component A | % Control Component B | % Control for Component A and B When Combined |
|---|---|---|---|---|
| Penoxsulam (A) + Dicamba (B) | 22.4 + 112 | 37 | 29 | 76 |
| Penoxsulam (A) + Dicamba (B) | 44.9 + 112 | 59 | 29 | 77 |

Post emergence greenhouse studies were conducted by applying a 0.14% w/w (weight for weight) penoxsulam loaded urea granule alone and in combination with commercial turf granules. The loading for the commercial granules is listed below Table XI. Greenhouse studies were applied on a kilogram of product per hectare basis (KG PR/Ha) post emergence to broadleaf weeds and sedge reared from seed or nutlet in 12.7" (32.25 cm) by 8.8" (22.35 cm) flats of a loam soil. Trial design was replicated block, one species per flat, 4 replicate flats per treatment. Post emergence applications were made to the flat covering both soil and misted foliage using a common hand-shaker method distributing the samples uniformly over the flat. Trial was sub-irrigated daily, and watered over the top 1 time per week starting 7 days after application to simulate a natural rainfall event. Active weed growth was maintained throughout the study period. Weed control was assessed at 2, 3 and 4 weeks after treatment. Control was determined visually by comparing treated and untreated flats and scored on a 0 to 100 percent scale where 0 corresponds to no control and 100 corresponds to complete kill.

Treatments, application rate employed and results for *Cyperus esculentus* (CYPES) are presented in the following Table XI.

TABLE XI

Postemergent Sedge (CYPES) Control 27 Days After Application
Penoxsulam + Commercial Turf Products Greenhouse Results

| Treatments | Rate in kg Product/Ha | % Control Component A | % Control Component B | % Control for Component A and B When Combined |
|---|---|---|---|---|
| Penoxsulam (A) + Scotts Plus 2 (B) | 2.4 + 70 | 16 | 25 | 50 |
| Penoxsulam (A) + Scotts Plus 2 (B) | 8.0 + 70 | 44 | 25 | 63 |
| Penoxsulam (A) + Momentum (B) | 2.4 + 88 | 16 | 4 | 30 |

TABLE XI-continued

Postemergent Sedge (CYPES) Control 27 Days After Application
Penoxsulam + Commercial Turf Products Greenhouse Results

| Treatments | Rate in kg Product/Ha | % Control Component A | % Control Component B | % Control for Component A and B When Combined |
|---|---|---|---|---|
| Penoxsulam (A) + Momentum(B) | 8.0 + 88 | 44 | 4 | 49 |

Components of each of the products:
Penoxsulam - 0.14% w/w urea granule
Scotts Plus 2 - 1.2% w/w 2,4-D + 0.6% mecoprop-P (29-3-4 NPK fertilizer granule)
Momentum Premium Weed & Feed - 0.57% 2,4-D + 0.057% triclopyr + 0.028% clopyralid (21-0-12 NPK fertilizer granule)

Pre-Emergent Activity of Penoxsulam Controlling Target Weeds in Orchard Floor

Pre-Emergence Applications of Penoxsulam for control of key orchard floor weed species were evaluated in the greenhouse and in the field.

Greenhouse studies were conducted by seeding species in a loam soil and applying the herbicides to the soil surface using a Cornwall 5 milliliter glass syringe fitted with a TeeJet TN-3 nozzle on an area basis. Immediately following herbicide application the pots were irrigated over the top to move the herbicides into the seeding zone. Pots were kept well irrigated throughout the trial. A percent visual weed control assessment was taken 4 weeks after application. Control was determined visually by comparing treated and untreated pots and scored on a 0 to 100 percent scale where 0 corresponds to no control and 100 corresponds to complete kill, or no emergence.

Field studies were conducted in a non-fumigated weed nursery trial. Weed species were planted in single strips with a row planter at 36 centimeter spacing. Plot size was 3.05×9.2 meters, 4 replicate plots per treatment. Weed species were seeded at appropriate depths and later the same day pre-emergent applications were made to the soil surface. Liquid applications were made using a backpack sprayer calibrated to deliver 187 liters per hectare (L/ha). Applications were made in Fresno, Calif. in June. Sprinkler irrigation was applied at regular intervals throughout study period. Control of each weed species in the study site was made 4 weeks after treatment. Control was determined visually by comparing treated and untreated weeds and scored on a 0 to 100 percent scale where 0 corresponds to no control and 100 corresponds to complete kill or no emergence.

Treatments evaluated, application rate employed, weed species evaluated and results are presented in the following Tables XII-XIII.

TABLE XII

Pre-emergent Percent Mean Control with Penoxsulam 28 Days After Application in the Greenhouse

| Treatment | Rate in gai/Ha | SINAR | EPHHE | EROCI | MALPA | MALNE | SONOL | SENVU |
|---|---|---|---|---|---|---|---|---|
| penoxsulam | 8.8 | 79 | 87 | 79 | 74 | 60 | 72 | 95 |
| penoxsulam | 17.5 | 91 | 97 | 97 | 87 | 92 | 78 | 100 |
| penoxsulam | 35 | 98 | 98 | 100 | 93 | 95 | 82 | 100 |
| penoxsulam | 70 | 98 | 100 | 100 | 100 | 98 | 87 | 100 |
| oryzalin | 400 | 60 | 60 | 93 | 70 | 53 | 92 | 32 |
| oryzalin | 800 | 90 | 68 | 100 | 77 | 77 | 97 | 40 |

TABLE XIII

Pre-emergent Percent Mean Control with Penoxsulam 27 Days After Application in a Weed Nursery in the Field

| Treatment | Rate in gai/Ha | AMARE | POROL | ECHCG | CYPES | SETFA | ECHCO |
|---|---|---|---|---|---|---|---|
| penoxsulam | 8.8 | 100 | 96 | 87 | 69 | 70 | 88 |
| penoxsulam | 17.5 | 100 | 97 | 96 | 81 | 78 | 94 |
| penoxsulam | 35 | 100 | 99 | 98 | 88 | 88 | 100 |
| penoxsulam | 70 | 100 | 100 | 100 | 94 | 96 | 100 |
| oryzalin | 2240 | 94 | 54 | 59 | 5 | 100 | 87 |
| oryzalin | 4480 | 100 | 84 | 87 | 27 | 100 | 89 |

What is claimed is:

1. A synergistic herbicidal composition comprising (a) penoxsulam and (b) a second herbicide or mixture of herbicides selected from the group of dicamba, the mixture of 2,4-D, triclopyr and clopyralid, or the mixture of 2,4-D and mecoprop-P.

* * * * *